United States Patent [19]

Ishii et al.

[11] Patent Number: 4,940,836

[45] Date of Patent: Jul. 10, 1990

[54] SOMATIC HYBRIDS OF RUTACEAE PLANTS

[75] Inventors: Shigetaka Ishii; Toshifumi Ohgawara, both of Noda; Shozo Kobayashi, Hiroshima; Iwao Oiyama, Hiroshima; Katsuichi Yoshinaga, Hiroshima, all of Japan

[73] Assignees: Director General of Fruit Tree Research Station Ministry of Agriculture, Forestry and Fisheries; Kikkoman Corporation, both of Japan

[21] Appl. No.: 782,385

[22] Filed: Oct. 1, 1985

[30] Foreign Application Priority Data

Feb. 20, 1985 [JP] Japan ................................... 60-30611

[51] Int. Cl.$^5$ ........................ A01H 1/04; C12N 15/00; C12N 5/00
[52] U.S. Cl. ................... 800/220; 435/172.2; 435/240.47; 435/240.51; 435/240.54; 935/94; 935/98; 800/DIG. 38; 800/DIG. 39
[58] Field of Search .................. 435/240, 241, 172.2; 935/89, 91, 94, 95, 96, 98; 800/1

[56] References Cited

PUBLICATIONS

Kobayashi et al. (1983) Japan Jour. Breed. 33:119–122.
Larkin et al. (1981) Theor. Appl. Genet. 60:197–214.
W. Handro (1981) in Ta Thorpe, ed., *Plant Tissue Culture, Methods and Applications in Agriculture,* Academic Press, NY, pp. 156–157.
Ohgawara et al. (1985) Theor. Appl. Genet, 71:1–4.
Gamborg et al. (1981) in TA Thorpe, ed., Plant Tissue Culture, Methods and Applications in Agriculture, Academic Press, NY, pp. 115–153.
Spiegel–Roy et al. (1980) Advances in Biochemical Engineering, vol. 16:29–48.
Button et al. (1977) in J. Reinert and YPS Bajai, eds. Plant Cell, Tissue, and Organ Culture, pp. 70–92.
T. Ohgawara et al., Theoretical and Applied Genetics, 1985, 71:1–4.
"Ribosomal DNA Analysis of Somatic Hybrids," T. Ohgawara, Plant Tissue Culture Letters, vol. 1, pp. 43–46, 1984.

*Primary Examiner*—Charles F. Warren
*Assistant Examiner*—Charles E. Cohen
*Attorney, Agent, or Firm*—Banner, Birch, McKie & Beckett

[57] ABSTRACT

Somatic hybrids of Rutaceae plants were obtained by allowing the protoplasts from embryogenic cells of a Rutaceae plant, which are of the nucellar origin, resistant to fusion treatment, and have a high proliferation activity, to fuse with the protoplasts of another Rutaceae plant having no proliferation activity, and then cultivating the fused protoplasts in a medium not containing a phytohormone but containing a saccharide in a concentration suitable for the selective embryogenesis of the hybrid cells.

11 Claims, No Drawings

SOMATIC HYBRIDS OF RUTACEAE PLANTS

BACKGROUND OF THE INVENTION

1. Field of the Invention

The present invention relates to somatic hybrids of Rutaceae plants and a production method thereof.

2. Description of the Prior Art

The cases of the production of somatic hybrids by cell fusion have heretofore been found in some plant families such as Solanaceae, Umbelliferae, and Cruciferae [Gleba and Hoffmann, Planta, 149, 112-117 (1980))], whereas none of the successful cases has been found in any Rutaceae plant, because the cell fusion treatments with polyethylene glycol or the like causes disorder of plant cells, or the production of somatic hybrids is unsuccessful owing to incompatibility between cells or the like, or the technique of selecting exclusively the hybrid cells has not yet been established. Furthermore, in the case of a Rutaceae plant, it was very difficult to produce a hybrid by conventional breeding, because of the phenomena of polyembryony, sterility, incompatibility, and the like. There is, therefore, a strong demand in the art for the development of a production means capable of efficiently and conclusively producing somatic hybrids of a Rutaceae plant.

SUMMARY OF THE INVENTION

Accordingly, it is an object of the present invention to provide new somatic hybrids of Rutaceae plants.

A further object is to provide a production method of somatic hybrids of Rutaceae plants using a cell fusion method.

A further object is to provide a culture medium which is capable of producing new somatic hybrids of Rutaceae plants selectively.

A further object is to provide a culture medium which is capable of producing new somatic hybrids of Rutaceae plants selectively.

Further objects of the invention will become apparent from the description of the invention which follows.

The present inventors carried out an extensive study on the method of producing somatic hybrids of Rutaceae plants by fusion treatment of protoplasts and, as a result, found that somatic hybrids of Rutaceae plants can be selectively and exclusively obtained by allowing the protoplasts of embryogenic cells of a Rutaceae plant, which are of nucellar origin, resistant to fusion treatment, and have a high proliferation activity, to fuse with the protoplasts of mesophyll cells or the like of other Rutaceae plant having no proliferation activity, and then cultivating the fused protoplasts in the absence of a phytohormone and presence of a saccharide such as sucrose or the like in a high concentration to suppress the embryogenesis of unfused embroygenic cells or of cells formed by fusion of embryogenic cells of nucellus origin themselves, except for the hybrid cells. The present invention has been accomplished on the basis of said discovery.

According to the present invention, there are provided somatic hybrids of a Rutaceae plant, a method for producing same and a culture medium used in producing same. The said method comprises cultivating an ovule of a Rutaceae plant in a customary plant tissue culture medium (a medium containing or not containing a phytohormone) to obtain cultured cells of nucellar origin, then subculturing said cultured cells in a medium containing a phytohormone to produce undifferentiated cells to fuse with the protoplasts derived from cultured cells having no or substantially no differentiation potency obtained by cultivating in a medium tissue cells or a tissue other than ovule of an other Rutaceae plant, and cultivating the resulting fused cells in a medium containing no phytohormone but containing a saccharide in a high concentration to effect embryogenesis of only the hybrid cells formed by the cell fusion, thereby to yield selectively the somatic hybrid cells of the Rutaceae plant.

DESCRIPTION OF THE PREFERRED EMBODIMENTS

The cultured cells of nucellus origin of a Rutaceae plant used in this invention are obtained by aseptically extracting the ovule from the flower within about eight weeks from the inflorescence and cultivating it by implanting on a common plant tissue culture medium. A stock culture of said cells, of course, can be used. As examples of the Rutaceae plants, mention may be made of orange, mandarin, grapefruit, and lemon.

As examples of the common plant tissue culture media, there may be mentioned Murashige and Skoog medium (MS medium; Physiol, Plant, 15, 473-497) and Murashige and Tucker medium [MT medium; Proc. First Int. Citrus Symp., Vol. 13, pp. 1155-1161 (1969)]. The media designated as "MT medium" and "MS medium" are those containing no phytohormone. In the ovule culture, MS or MT medium can be used as such or, if necessary, after addition of a phytohormone such as 6-benzylaminopurine or the like; a malt extract or adenine sulfate can be added, too.

The cultivation is carried out under weak light for 2 to 5 months.

The cultured cells of nucellar origin are then subcultured in a medium containing a phytohormone, such as an agar medium or a liquid medium containing one or more phytohormones such as cytokinin, auxin, gibberellin, and the like, thereby to produce undifferentiated cells, the embryogenesis being suppressed. The cultivation is carried out preferably at about 20° to 30° C. under a weak light, the transfer to fresh medium being done about every 4 weeks in the case of an agar medium and every about 2 weeks when liquid media are used. The separation of the undifferentiated cells is performed by filtration using, for example, a metal or nylon gauze.

The embryogenic cells resistant to cell fusion treatment are obtained by cultivating the above undifferentiated cells in a common plant tissue culture medium containing no phytohormone, for example, MT medium or modified MT medium, in which the modification being made by replacing the sucrose, a saccharide constituent of MT medium, with galactose or lactose, or further addition of a reductive nitrogen such as ammonium ion, thereby to induce and accelerate the embryogenesis. The cultivation is carried out in either a liquid or solid medium and the period of cultivation ,is about 2 to 4 weeks. After completion of the cultivation, the cells are separated from the culture, then transplanted in a fresh medium of the same composition, and cultivated for 3 to 7 days. The embryogenic cells can be separated in a customary manner from the culture mixture.

The protoplasts are prepared from the above embryogenic cells by the action of a maceration enzyme and a cell wall degrading enzyme upon said cells in a dark place at about 20° to 30° C. for about 5 to 16 hours with mild shaking, then followed by filtration and centrifugtaion. As examples of the maceration enzymes, mention may be made of Pectolyase Y-23 (Seishin Pharmaceutical Co) and Macerozyme R-10 (Yakult Pharmaceutical Industry Co.). As the cell wall degrading enzyme, use may be made of Cellulase Y-C (Seishin Pharmaceutical Co.), Cellulose Onozuka R-10 (Yakult Pharmaceutical Industry Co.), Cellulose Onozuka RS (Yakult Pharmaceutical Industry Co.), and Dricelase (Kyowa Hakko Kogyo Co.). The enzyme solution is prepared in a customary manner. The filtration is performed by means of a metal or nylon gauze; Miracloth (Calbiochem-Behring Corp., USA) is generally used. The protoplasts of embryogenic cells obtained by centrifugation are used as a suspension in about 0.6 M mannitol solution.

A description is given below of the procedure of preparing protoplasts, which are to be fused with the above-mentioned protoplasts, from cultured cells having no or substantially no differentiation potency obtained by cultivating in a medium tissue cells or a tissue other than the ovule of an other Rutaceae plant. Protoplasts are prepared from the cultivated cells having no or substantially no differentiation potency, which are obtained by implanting the tissue cells or a tissue other than ovule of a Rutaceae plant in a suitable agar medium and cultivating. As examples of Rutaceae plants, there may be mentioned trifoliate orange, Troyer citrange, orange, mandarin, grapefruit, and lemon. The tissue cells used are of root or leaf origin. The protoplast suspension is prepared by the same treatment as that used in preparing the suspension of ptoroplasts of embryogenic cells. When the tissue cells are used, the tissues, if necessary, are sterilized with a 70 vol.% ethanol solution, then immersed in a suitable sterilizing solution such as, for example, a sodium hypochlorite solution containing Tween 20, and washed with sterile water.

The fusion is carried out in the presence of suitable chemical substances using a suspension of the protoplasts from embryogenic cells of the nucellus origin and a suspension of the protoplasts from tissue cells or cultivated cells, the cell concentration of each suspension having been adjusted to about $10^5$–$10^6$/ml. As examples of the chemical substances, mention may be made of polyethylene glycol and polyvinyl alcohol. These chemical substances are used in the form of solution and, if necessary, calcium ion is added. The solution in an amount approximately equal to that of the mixture of both protoplast suspensions is added to the latter. The resulting mixture is left standing for about 10 to 15 minutes and admixed with a mannitol solution containing calcium ion to effect the fusion.

The solution containing the fused protoplasts thus obtained is centrifuged to collect the total protoplasts. The total protoplasts are washed with a mannitol solution and subjected to liquid or solid cultivation in a medium containing no phytohormone but containing a saccharide such as sucrose, glucose, fructose, or the like, which suppresses the induction of embyrogenesis or growth of the cells such as those that orignated from the nucleus, in a concentration capable of evoking said suppressing effects; the concentraiton of the saccharide is preferably 0.4 to 0.6 M. The cultivation is carried out at a cell concentration of $10^4$–$10^5$/ml and under weak light or in the dark at about 20° to 30° C. In the case of liquid cultivation, after 3 to 4 weeks from the beginning of cultivation, preferably an agar medium containing no phytohormone but containing about 0.3 M saccharide is added to the medium and the cultivation is continued. In the case of solid medium, about 1 month from the beginning of containing 5% by weight of sucros is added and the cultivation is continued, while a small amount of said liquid medium being added approximately monthly. After 2 to 3 weeks from the beginning of cultivation, it is preferable to continue the cultivation under exposure to light at about 3,000 lux. After 2 to 3 months of cultivation, only the hybrid cells undergo embryogenesis to form embryoids. Somatic hybrids are obtained by cultivating the embryoids in a medium containing no phytohormone but containing a malt extract, adenine sulfate, and the like, and transferring the grown embryoids to a medium containing gibberellin to cause rooting and shooting.

As described above, according to this invention somatic hybrids of Rutaceae plants having those genetic characteristics which are unobtainable by means of crossing can be efficiently and assuredly obtained.

Examples of embodiments of this invention are described below, but the invention is not limited thereto.

EXAMPLE 1

As a source of undifferentiated cells, a tissue culture obtained in the following manner was employed. Ovules had been collected aseptically by means of a pair of tweezers from the flowers of Trovita orange plants on the first day of blooming and implanted in an MT agar medium containing malt extract (100 mg/liter) and adenine sulfate (20 mg/liter). The cultivated cells of nucellus origin obtained after 150 days of cultivation had been further held for about 5 years in an MT agar medium containing 10 mg/liter of 6benzylaminopurine, a phytohormone, to proliferate.

A portion of the undifferentiated cells thus stored was transferred to a liquid medium containing 10 mg/liter of 6-benzylaminopurine and subcultured for about one year. The culture mixture was filtered through a nylon gauze to collect undifferentiated cells.

The undifferentiated cells obtained above were then cultured in an MT liquid medium for two weeks, then transferred to a medium of the aforementioned composition, and subcultured for 5 days to produce embryogenic cells. About 1 g of the embryogenic cells collected by filtering the culture mixture through Miracloth was immersed in 20 ml of a sterile enzyme solution [an aqueous enzyme solution containing 0.3% (W/V) of macerozyme R-10 (Yakult Pharmceutical Industry Co.), 0.2% (W/V) of Cellulase Onozuka R-10 (Yakult Pharmaceutical Industry Co.), 0.1% (W/V) of Driselase (Kyowa Hakko Kogyo Co.), 0.15 M sucrose, 0.56 M mannitol, and macro inorganic constituents of MT medium]and agitated by revolution at 45 rpm for 1.6 hours in the dark to produce protoplasts. The protoplasts were filtered thorugh Miracloth, centrifuged at 800 rpm for 5 minutes, and suspended in a 0.6 M mannitol solution to obtain a suspension of protoplast of Trovita orange plant.

On the other hand, trifoliate orange seeds were sown in vermiculite and left for about 2 months at 25° C. under 16 hours/day illumination at 3,000 lux to obtain trifoliate orange seedlings. The leaves of these seedlings were washed with a 70% (V/V) ethanol for 10 seconds, then immersed for 20 minutes in a 0.5% (V/V) aqueous sodium hypochlorite solution containing 0.1% of Tween 20, and washed with sterile water. The leaves were cut with a razor blade at an interval of 2 mm and dipped for 1 hour in an MES [2-(N-morpholino) ethanesulfonic acid monohydrate]buffer (pH 5.8). Thereafter, a small piece (0.6 g) of the leaf was immersed in 20 ml of a sterile enzyme solution [a 1 mM MES buffer (pH 5.8) containing 0.3% (W/V) of Macerozyme R-10, 3% (W/V) of Cellulase Onozuka R-10, 0.6 M mannitol, and macro inorganic constituents of MT medium]and agitated by revolution at 45 rpm for 16 hours in a dark place, thereby to obtain protoplasts. The protoplasts were filtered through Miracloth, then centrifuged at 800 rpm for 2 minutes, and suspended in a 0.6 M mannitol solution to obtain a suspension of the protoplasts of trifoliate orange.

Both suspensions of Trovita orange protoplast and trifoliate orange protoplasts were each adjusted to a cell concentraiton of $10^6$/ml and mixed together each 200 μl of the mixed protoplast suspension was placed in a plastic dish, 6 cm in diameter. To the area surrounding the protoplast suspension, was added 200 μl of an aqueous PEG solution [pH 6.5; an aqueous solution containing 40% (W/V) polyethylene glycol, 100 mM calcium chloride, and 100 mM HEPES (N-2-hydroxyethylpiperazine N'-2-ethanesulfonic acid) buffer]. The suspension and the solution were gently mixed and left standing for 10 minutes. To the mixture, was added gently 0.5 ml of a washing solution (an aqueous solution containing 50 mM calcium chloride and 0.6 M mannitol) to facilitate the fusion of both protoplasts. Then, 1 ml of the washing solution was gently added twice at an interval of 15 minutes. After 15 minutes, the suspension was diluted with about 2 ml of a 0.6 M mannitol solution and the diluted suspension was transferred to the centrifuge tubes and centrifuged at 1,000 rpm for 5 minutes to collect the fused protoplasts.

The fused protoplasts obtained above were washed twice with 0.6 M mannitol solution by repeating the centrifuging at 1,000 rpm for 5 minutes. The fused protoplasts were further washed with an MT medium containing 0.6 M sucrose by centrifuging in the same manner as described above. The washed protoplast suspension was adjusted to a cell density of $10^5$/ml. Into a dish of 6 cm in diameter, was added 0.5 ml of the above cell suspension, sealed with Parafilm (American Can Co.), and cultivated under a weak light at 24° to 27° C. After 3 weeks from the beginning of the cultivation, 1 ml of an MT agar medium containing 5% of sucrose and 1.2% (W/V) of agar was added to the medium and cultivation was continued. The embryoids obtained after 2 months were transferred to an MT agar medium containing a malt extract (500 mg/liter) and adenine sulfate (40 mg/liter) to proliferate and subsequently transferred to an MT agar medium containing gibberellin (10 mg/liter), to obtain a plant. This plant was presumed to be a hybrid, because it showed morphological characteristics intermediate between those of Trovita orange and trifoliate orange and had chromosome numbers of 36 which were the sum of those of parents (2n =18). Moreover, it was confirmed to be a somatic hybrid of Trovita orange and trifoliate orange, because it possessed characteristics of both parents, as evidenced by the analysis of ribosomal RNA genes and the essential oil of the leaves.

EXAMPLE 2

The same tissue culture as Example 1 was employed. Ovules had been collected aseptically by means of a pair of tweezers from the flower of Trovita orange plant on the first day of blooming and implanted in an MT agar medium containing malt extract (100 mg/liter) and adenine sulfate (20 mg/liter). The cultivated cells of nucellus origin obtained after 150 days of cultivation had been further held for about 5 years in an MT agar medium containing 10 mg/liter of 6-benzylaminopurine, a phytohormone, to continue multiplication.

A portion of the undifferentiated cells thus stored was transferred to a liquid medium containing 10 mg/liter of 6-benzylaminopurine and subcultured for about one year. The culture mixture was filtered through a nylon gauze to collect undifferentiated cells.

The undifferentiated cells obtained above were then cultured for 2 weeks in an MT liquid medium containing 5% (W/V) galactose in place of sucrose, then transferred to a medium of the aforementioned composition, and subcultured for 5 days to produce embryogenic cells. About 1 g of the embryogenic cells collected by filtering the cultured mixture through Miracloth was immersed in 20 ml of a sterile enzyme solution [an aqueous enzyme solution containing 0.3% (W/V) of Macerozyme R-10, 0.2% (W/V) of Cellulase Onozuka R-10, 0.1% (W/V) of Driselase, 0.14 M sucrose, 0.56 M mannitol, and macro inorganic constituents of MT medium]and agitated by revolution at 45 rpm for 16 hours in the dark to produce protoplasts. The protoplasts were filtered through Miracloth, centrifuged at 800 rpm for 5 minutes, and suspended in a 0.6 M mannitol solution to obtain a suspension of protoplasts of Trovita orange plant.

On the other hand, seedlings of Troyer citrange were bred in a greenhouse under natural light for about one year. The well grown young leaves of the plant wer washed with 70% (V/V) ethanol for 10 seconds, then dipped in a 0.5% (V/V) aqueous sodium hypochlorite solution containing 0.1% of Tween 20 for 20 minutes, then washed with sterile water, and cut with a razor blade at an interval of 2 mm. The cut leaves were immediately dipped for 1 hour in 1 mM MES buffer (pH 5.8) containing 0.6 M mannitol, and macro inorganic constituents of MT medium. After dipping, 1.0 g of small pieces of the cut leaves were immersed in 20 ml of a sterile enzyme thyme solution [a 1 mM MES buffer (pH 5.8) containing 0.3% (W/V) of Macerozyme R-10, 3% (W/V) of Cellulase Onozuka R-10, 0.6 M mannitol, and macro inorganic constituents of MT medium]and agitated by revolution at 45 rpm for 16 hours in the dark, thereby to produce protoplasts. The protoplasts were filtered through Miracloth, then centrifuged at 800 rpm for 5 minutes, and suspended in a 0.6 M mannitol solution to prepare a suspension of protoplasts of Troyer citrange.

Suspensions of both Trovita orange protoplast and Troyer citrange protoplasts were each adjusted to a cell density of $10^6$/ml and mixed together. Each 200 μl of the mixed protoplast suspension was placed in a plastic Petri dish, 6 cm in diameter. To the area surrounding the protoplast suspension, was added 200 μl of an aqueous PEG solution [pH 6.5; an aqueous solution containing 40% (W/V) polyethylene glycol, 100 mM calcium chloride, and 100 mM HEPES buffer]. The suspension and the solution were gently mixed and left standing for 10 minutes. To the mixture, was added gently 0.5 ml of a washing solution (an aqueous solution 50 mM calcium chloride and 0.6 M mannitol) to facilitate the fusion of both protoplasts. Then 1 ml of the washing solution was gently added twice at an interval of 15 minutes. After 15 minutes, the suspension was diluted with about 2 ml of a 0.6 M mannitol solution and the diluted protoplast suspension was transferred to centrifuge tubes and centrifuged at1,000 rpm to collect fused protoplasts.

The fused protoplasts obtained above were washed twice with a 0.6 M mannitol solution by repeating the centrifuging at 1,000 rpm for 5 minutes. The fused protoplasts were further washed with an MT medium containing 0.6 M sucrose by centrifuging in the same manner as described above. The washed protoplast suspension was adjusted to a cell density of $10^5$/ml. To 0 1 ml of this cell suspension, was added 1 ml of an MT medium containing 0.6 M of sucrose and 1.2% Seaplaque agarose (Marine Colloid Co.). The cell suspension was then placed in a Petri dish, 6 cm in diameter, sealed with Parafilm, and cultivated at 24° to 27° C. under a weak light. After 4 weeks from the beginning of cultivation, 500 μl of an MT liquid medium was added to the dish and cultivation was continued. The embryoids obtained after 2 months were transferred to an MT agar medium containing a malt extract (500 mg/liter) and adenine sulfate (40 mg/liter) to effect proliferation. The embryoids were subsequently transferred to an MT medium containing gibberellin (10 mg/liter to obtain a plant.

EXAMPLE 3

As a source for the undifferentiated cells, the tissue culture prepared in the following manner was employed. Ovules had been collected aseptically by means of a pair of tweezers from the flower of Bahia navel orange plant on the first day of blooming and implanted in an MT agar medium containing a malt extract (100 mg/liter) and adenine sulfate (20 mg/liter). The cultivated cells of nucellar origin obtained after 100 days of cultivation had been further held for about 3 years in an MT agar medium containing 10 mg/liter of 6benzylaminopurine, a phytohormone, to effect proliferation.

A portion of the undifferentiated cells thus stored was transferred to a liquid medium containing 10 mg/liter of 6-benzylaminopurine and subcultured for about two months. The culture mixture was filtered through a nylon gauze to collect undifferentiated cells.

The undifferentiated cells obtained above were then cultured in an MT liquid medium containing 5% (W/V) of galactose in place of sucrose for 2 weeks, then transferred to a medium of aforementioned composition, and after 2 weeks of cultivation, was subcultured for 5 days to produce embryogenic cells. About 1 g of the embryogenic cells collected by filtering the culture mixture through Miracloth was immersed in 20 ml of a sterile enzyme solution [an aqueous enzyme solution containing 0.3% (W/V) of Macerozyme R-10, 0.2% (W/V) of Cellulase Onozuka R-10, 0.1% (W/V) of Driselase, 0.14 M of sucrose, 0.56 M of mannitol, and macro inorganic constituents of MT medium.]and agitated by revolution at 45 rpm for 16 hours in the dark to produce protoplasts. The protoplasts were filtered through Miracloth, centrifuged at 800 rpm for 5 minutes, and suspended in a 0.6 M mannitol solution to obtain a suspension of protoplasts of Bahia navel orange plant.

On the other hand, seedlings of Troyer citrange were bred in a greenhouse under natural light for about one year. The well grown young leaves of the plant were washed with 70% (V/V) ethanol for 10 seconds, then dipped in a 0.5% (V/V) aqueous sodium hypochlorite solution containing 0.1% of Tween 20 for 20 minutes, then washed with sterile water, and cut with a razor blade at an interval of 2 mm. The cut leaves were immediately dipped for 1 hour in a 1 mM MES buffer (pH 5.8) containing 0.6 M of mannitol, and macro inorganic constituents of MT medium. After dipping, 1.0 g of small pieces of the cut leaves was immersed with 20 ml of a sterile enzyme solution [a 1 mM MES buffer (pH 5.8) containing 0.3% (W/V) of Macerozyme R-10, 3% (W/V) of Cellulase Onozuka R-10, 0.6 M of mannitol, and macro inorganic constituents of MT medium]and agitated by revolution at 45 rpm for 16 hours in the dark, thereby to produce protoplasts. The protoplasts were filtered through Miracloth, then centrifuged at 800 rpm for 5 minutes, and suspended in a 0.6 M mannitol solution to prepare a suspension of protoplasts of Troyer citrange.

Both suspensions of Bahia navel orange protoplasts and Troyer citrange protoplasts were each adjusted to a cell density of $10^6$/ml and mixed together. Each 200 μl of the mixed protoplast suspension was placed in a plastic Petri dish, 6 cm in diameter. To the area surrounding the protoplast suspension, was added 200 μl of an aqueous PEG solution [pH 6.5; an aqueous solution containing 40% (W/V) of polyethylene glycol, 100 mM calcium chloride, and 100 mM HEPES buffer]. The suspension and the solution were gently mixed and left standing for 10 minutes. To the mixture, was added gently 0.5 ml of a washing solution (an aqueous solution containing 50 mM calcium chloride and 0.6 M mannitol) to effect the fusion of both protoplasts. Then 1 ml of the washing solution was gently added twice at an interval of 15 minutes. After 15 minutes, the suspension was diluted with about 2 ml of 0.6 M mannitol solution and the diluted protoplast suspension was transferred to centrifugal tubes and centrifuged at 1,000 rpm to collect fused protoplasts.

The fused protoplasts obtained above were washed twice with a 0.6 M mannitol solution by repeating the centrifuging at 1,000 rpm for 5 minutes. The fused protoplasts were further washed with an MT medium containing 0.6 M of sucrose by centrifuging in the same manner as described above. The washed protoplast suspension was adjusted to a cell density of $2 \times 10^5$/ml. To 1 ml of this cell suspension, was added 1 ml of an MT medium containing 0.6 M sucrose and 1.2% Seaplaque agarose (Maine Colloid Co.). The cell suspension was then placed in a Petri dish, 6 cm in diameter, sealed with Parafilm, and cultivated at 24° to 27° C. under weak light. After 4 weeks from the beginning of cultivation, 500 μl of an MT liquid medium was added to the dish and cultivation was continued. The embryoids obtained after 2 months were transferred to an MT agar medium containing a malt extract 500 mg/liter) and adenine sulfate (40 mg/liter) to effect proliferation. The embryoids were further transferred to an MT medium containing gibberellin (10 mg/liter),hereby to obtain a plant.

We claim:

1. Somatic hybrid plants of the Rutaceae family produced by fusing (A) first protoplasts of embryogenic cells resistant to fusion treatment and having a high proliferation activity, said first protoplasts being derived by the cultivation of undifferentiated cells obtained from subculture of cultivated cells originated from the nucellus of a first plant of the Rutaceae family with (B) second protoplasts derived from cultivated cells having no differentiation potency, said second protoplasts originated from tissue cells or tissues other than the ovules of a second plant of the Rutaceae family to form fused cells, and cultivating the fused cells in a medium containing sucrose in a concentration sufficient for the selective embryogenesis of the fused cells said first and second plants being selected from two different species.

2. Somatic hybrid plants of the Rutaceae family according to claim 1, wherein the first plant of the Rutaceae family providing nucellar protoplasts is orange, mandarin, grapefruit, or lemon.

3. Somatic hybrid plants of the Rutaceae family according to claim 2, wherein the second plant of the Rutaceae family providing non-ovule derived protoplasts is trifoliate orange, Troyer citrange, orange, mandarin, grapefruit, or lemon.

4. A method for producing somatic hybrid plants of the Rutaceae family which comprises the steps in sequence of:
   (1) subculturing cells derived from the nucellus of a first plant of the Rutaceae family in a medium containing a phytohormone, thereby to produce undifferentiated cells;
   (2) cultivating the resulting undifferentiated cells in a medium for plant tissue culture, thereby to produce embryogenic cells and producing protoplasts from said embryogenic cells;
   (3) obtaining protoplasts from cultivated cells having no differentiation potency, by cultivating in a medium tissue cells or tissues other than ovules of a second plant of the Rutaceae family;
   (4) fusing said protoplasts of the second plant with the protoplasts of the embryogenic cells of the first plant obtained in step (2) to obtain fused protoplasts; and
   (5) cultivating the fused protoplasts in a medium without phytohormones but containing sucrose in a concentration sufficient for the repression of embryogenesis of nucellar protoplasts and for the selective embryogenesis of the fused hybrid cells, thereby to produce selectivity somatic hybrid plants.

5. A method for producing somatic hybrid plants of the Rutaceae family according to claim 4 wherein the concentration of sucrose is 0.4 to 0.6 M.

6. A method for producing somatic hybrid plants of the Rutaceae family according to claim 4, wherein the first plant of the Rutaceae famile is selected from the group consisting of orange, mandarin, grapefruit, or lemon.

7. A method for producing somatic hybrid plants of the Rutaceae family according to claim 6, wherein the second plant of the Rutaceae family is selected from the group consisting of trifoliate orange, Troyer citrange, orange, mandarin, grapefruit, or lemon, and wherein the first and second plants are selected from two different species.

8. A method for producing somatic hybrid plants of the Rutaceae family according to claim 5 or 7, wherein the phytohormone in the subculture medium is one or more of cytokinin, auxin, and gibberellin.

9. A method for producing somatic hybrid plants of the rutaceae family according to claim 8, wherein the subculturing of step (1) is carried out at 20° to 30° C. under weak light.

10. A method for producing somatic hybrid plants of theRutaceae family according to claim 9, wherein the subculturing of step (1) is carried out in a liquid culture medium.

11. A culture medium for the production of somatic hybrid plant of the Rutaceae family, which contains no phytohormone and comprises 0.4 to 0.6 M sucrose for the repression of embryogenesis of nucellar protoplasts and the selective embryogenesis of fused hybrid cells.

* * * * *